(12) United States Patent
Assell et al.

(10) Patent No.: US 7,717,919 B2
(45) Date of Patent: May 18, 2010

(54) APPLICATION OF THERAPY ALIGNED TO AN INTERNAL TARGET PATH

(75) Inventors: Robert L. Assell, St. Paul, MN (US); Eugene A. Dickhudt, Lino Lakes, MN (US)

(73) Assignee: TranS1 Inc., Wilmington, NC (US)

( * ) Notice: Subject to any disclaimer, the term of this patent is extended or adjusted under 35 U.S.C. 154(b) by 782 days.

(21) Appl. No.: 11/593,445

(22) Filed: Nov. 6, 2006

(65) Prior Publication Data

US 2007/0112351 A1    May 17, 2007

Related U.S. Application Data

(60) Provisional application No. 60/733,436, filed on Nov. 4, 2005.

(51) Int. Cl.
*A61B 17/58* (2006.01)
*A61B 17/60* (2006.01)
*A61F 2/00* (2006.01)

(52) U.S. Cl. ............... 606/96; 606/97; 606/98; 606/247; 606/59

(58) Field of Classification Search ........... 606/96–98, 606/54, 59, 247; 408/69–71, 150, 159, 187, 408/236
See application file for complete search history.

(56) References Cited

U.S. PATENT DOCUMENTS 3,837,505 A    9/1974  Muggli ............... 214/6 BA
4,257,411 A *  3/1981  Cho .................... 606/96
5,514,144 A    5/1996  Bolton ................ 606/96
6,440,139 B2   8/2002  Michelson ............ 606/80
6,547,795 B2 * 4/2003  Schneiderman ........ 606/96
7,396,360 B2 * 7/2008  Lieberman ........... 606/247
2006/0079908 A1 4/2006 Lieberman .......... 606/86 A
2006/0085010 A1 4/2006 Lieberman ........... 606/61

FOREIGN PATENT DOCUMENTS

WO    WO 2006/038957 A1    4/2006
WO    WO 2006/038959 A1    4/2006

OTHER PUBLICATIONS

International Search Report and Written Opinion From Corresponding PCT Application No. PCT/US2006/043363, Sep. 13, 2007 (9 pgs).

\* cited by examiner

*Primary Examiner*—Thomas C Barrett
*Assistant Examiner*—Andrew Yang
(74) *Attorney, Agent, or Firm*—The Eclipse Group LLP; Kevin E. Flynn

(57) ABSTRACT

An alignment jig that creates a plurality of parallelograms may be used to align an external alignment line with an internal target path. The internal target path is within the patient's body and may be defined by two guide pin tips. The alignment jig may be created so that it creates the external alignment line to be co-linear with the internal target path or the external alignment line may be parallel to the internal target path by offset a distance from being co-linear. The external alignment line may be used in the provision of therapy such as the delivery of a screw to a precise location in the provision of therapy to a portion of the spine.

14 Claims, 14 Drawing Sheets

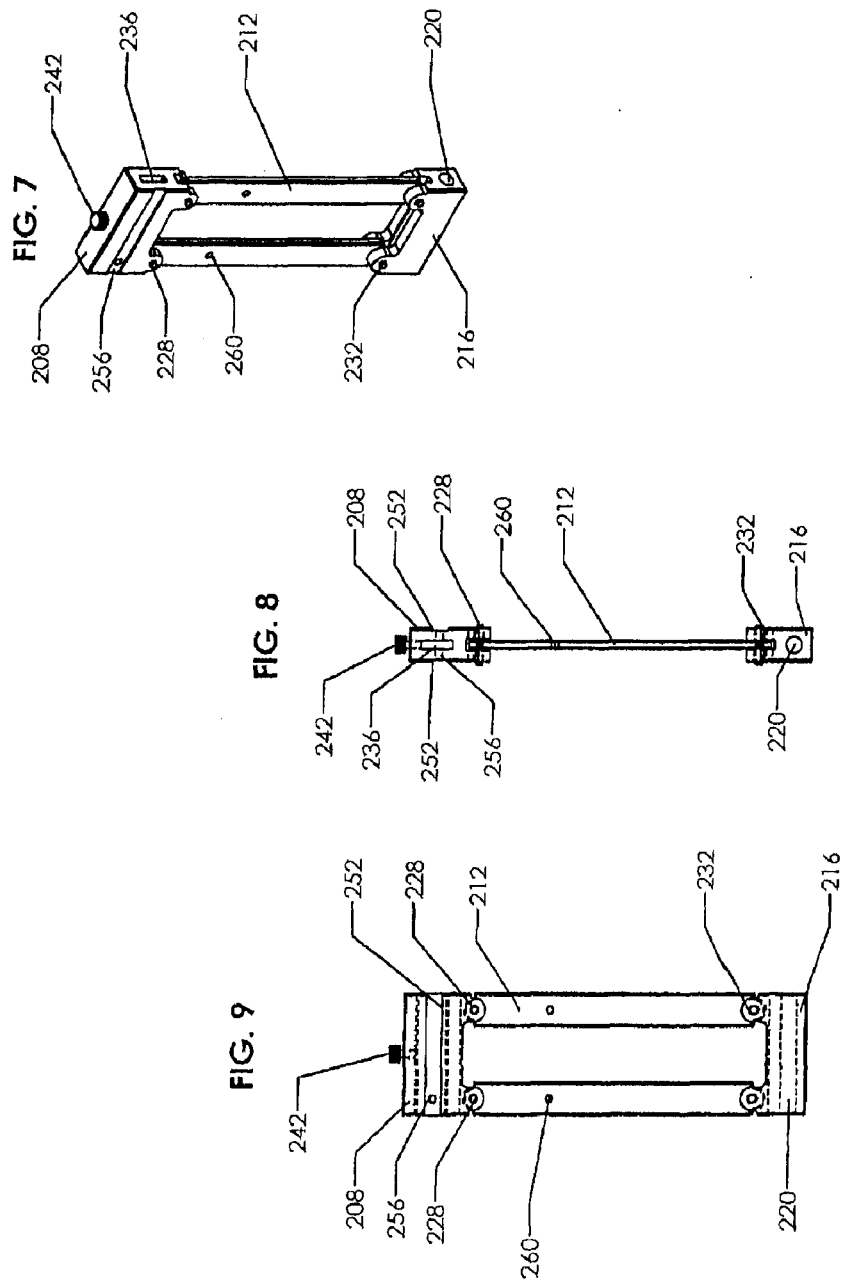

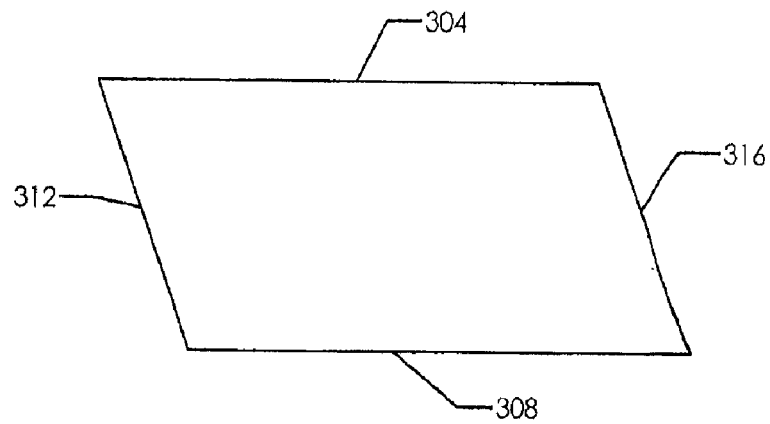
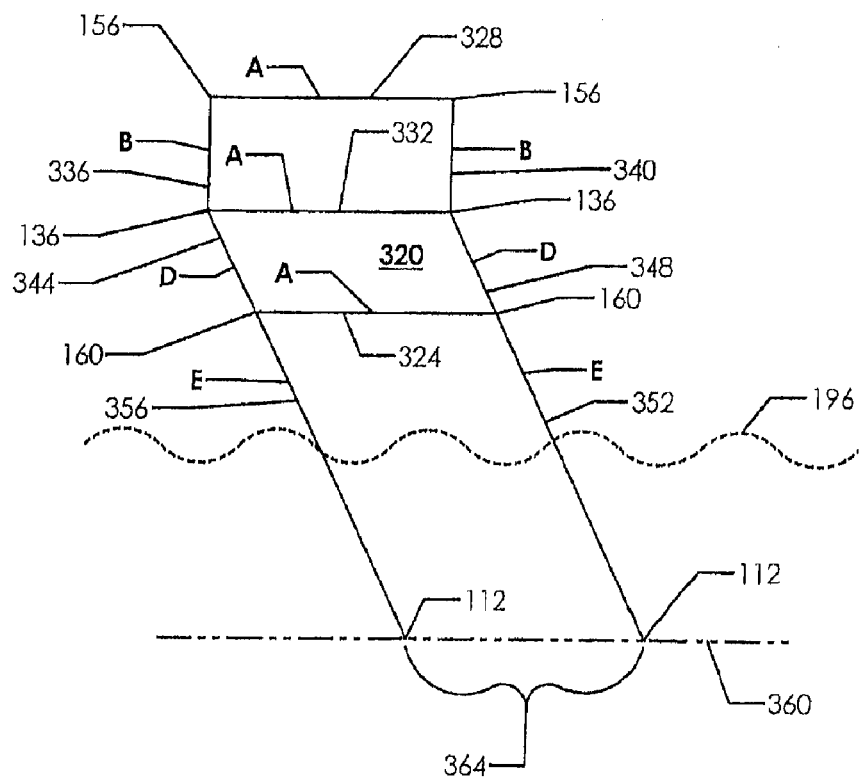

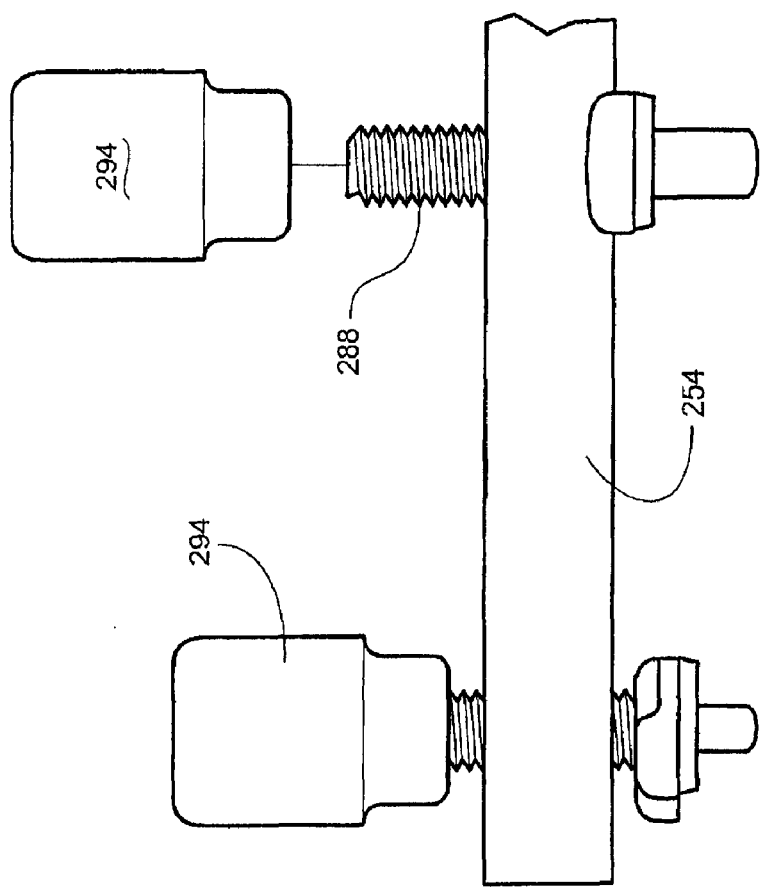
FIG. 15
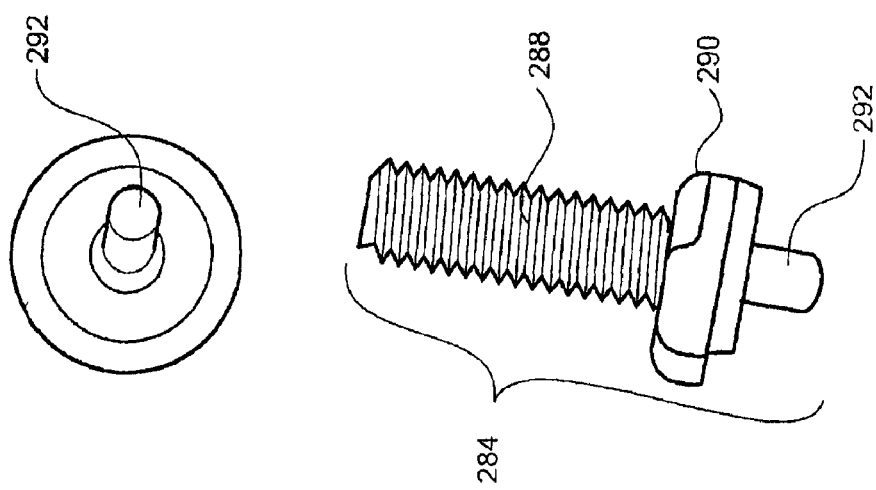

APPLICATION OF THERAPY ALIGNED TO AN INTERNAL TARGET PATH

This application claims priority and incorporates by reference herein a provisional application filed on Nov. 4, 2005 for Method & Apparatus for Fixation of Adjacent Vertebrae, United States Provisional Patent Application No. 60/733,436.

BACKGROUND OF THE INVENTION

1. Field of Invention

This invention relates generally to medical procedures and in particular, minimally invasive medical procedures. One application of the present invention is in providing therapy to adjacent spinal vertebrae. More specifically, one application that uses the alignment jig is the facilitation of the reproducible deployment and placement of fixation device such as a screw, via an aligned, percutaneous access and approach, designed to relieve lower back pain and possibly improve disc health and prevent progression or transition of disease.

2. Problem Addressed

Some medical procedures require the application of a particular therapy in a particular place and inadvertent application of what was intended to be therapeutic intervention to a place within the body close to but different from the particular place can be undesirable. The need for precise placement of therapy is particularly important when working with the spinal column as is may be desirable to place a bone screw into adjacent bone segments to immobilize a portion of the spinal column but it would be undesirable to place the same screw into any other portion of the spine or spinal cord.

The application of therapy through minimally invasive procedures has many benefits for the patient but adds challenges to the surgeon seeking to deliver therapy to a specific location while working primarily outside of the body and accessing the site to receive therapy by limited access routes such as one or more percutaneous working cannula. The problem is made more difficult by the variations in patient anatomy as work on a particular patient in one specific portion of the particular patient's spinal column will not have the same exact dimensions and relationships between components in the spinal column as doing the same procedure on another patient.

The surgeon or other provider of medical therapy may rely on the general properties of human anatomy and on the benefits afforded by real-time imaging of the anatomy and any inserted instruments. For example, the surgeon may use one or more imaging devices to obtain fluoroscopic guidance to help maintain anterior/posterior and lateral alignment.

Turning to FIG. 1, the problem can be summarized as follows. A surgeon can locate the structures of interest in the patient's body 10 beneath the skin even in a minimally invasive procedure. With knowledge of anatomy and the desired therapy, the surgeon discerns the desired internal target path 20. The prior art has not provided a solution that allows the surgeon to translate the internal target path 20 to outside of the patient with adequate precision to allow the surgeon to confidently align the delivery of therapy (external alignment line 30) with the desired internal target path 20 plus whatever offset from co-linear 40 is desired. Sometimes it is useful to have some non-zero offset 40 from co-linear so that the delivery of therapy does not strike markers 50 inserted by the surgeon as part of the process of defining the internal target path 20.

Any tool or process to be used by a surgeon benefits from being easy to use even while gloved and wearing gloves that may be wet. A tool or process that requires a surgeon to use an assistant as the process cannot be completed with only two hands would be less desirable than a process that may be done with two or fewer hands. A tool or process that reduces the need for mental steps such as calculations and measurements, reduces possible sources of error for the process.

SUMMARY

An alignment jig that creates a plurality of parallelograms may be used to align an external alignment line with an internal target path. The internal target path is within the patient's body and may be defined by two guide pin tips. The alignment jig may be assembled so that it creates the external alignment line to be co-linear with the internal target path or the external alignment line may be parallel to the internal target path by offset a distance from being co-linear. The external alignment line may be used in the provision of therapy such as the delivery of a screw to a precise location in the provision of therapy to a component in the spine.

BRIEF DESCRIPTION OF THE FIGURES

FIG. 7 is a perspective view of a swivel cannula guide assembly 204.

FIG. 8 is a side view of a swivel cannula guide assembly 204.

FIG. 9 is a front view of a swivel cannula guide assembly 204.

FIG. 10 is a parallelogram.

FIG. 11 shows a first parallelogram 320 that is created while using an alignment jig.

FIG. 15 contains several views of a stud assembly 280.

DETAILED DESCRIPTION

Figure 1:
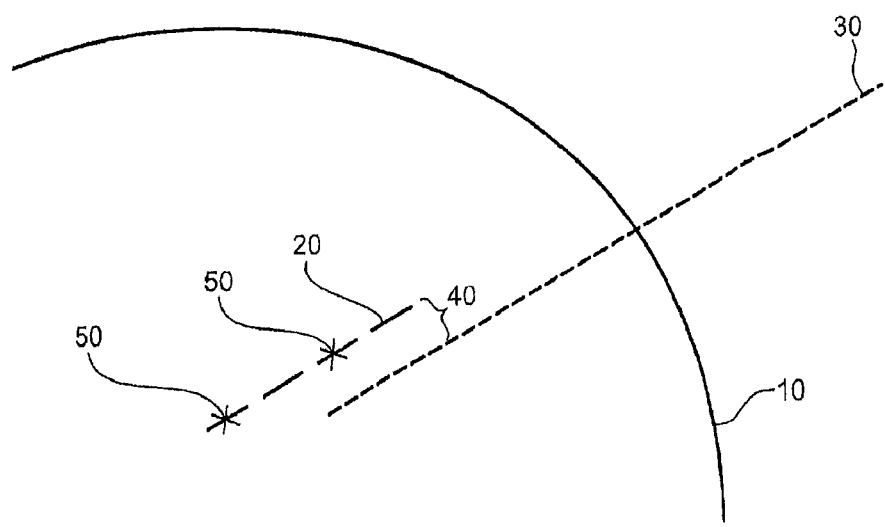
FIG. 1 illustrates the concepts of an internal target path and an external alignment line as part of describing the problem addressed by the present disclosure.

As is often the case when attempting to convey an creative concept that may be implemented in many different ways, it is useful to start with a concrete example of one specific implementation so that the concepts of operation may be tangibly conveyed. The effort to provide one or more tangible examples in order to promote the understanding of the present invention should not be misinterpreted as a limitation on the scope of the invention as the scope of the invention is set forth in the claims that follow this disclosure.

Before starting with the description it is useful to review the meanings of the terms co-linear and parallel as those terms appear in the specification below. A line is co-linear with another line if an extension of the line contains the second line. A line is parallel with another line is the two lines have the same slope in the same plane and do not intersect. Using these definitions, a co-linear pair of lines are not a special case of parallel lines as they do intersect and thus are not parallel.

In the practical world, the two concepts of co-linear and parallel can be said to be different instances of offsets from co-linear. A pair of parallel lines have the same slope and exist in the same plane but have a non-zero offset from one another. A pair of lines that are actually co-linear have the same slope and exist in the same plane (actually in an infinite number of planes) but the have an offset of zero from co-linear.

While the terms co-linear and parallel have precise definitions from the theoretical field of geometry, the terms co-linear and parallel are intended to be interpreted in this specification and the claims that follow in a practical or clinical sense. In other words, when delivering therapy, is the external alignment line established so that the therapy is delivered essentially co-linear or parallel with the internal markers defining an internal target path. Chances are good that these two lines will not meet the theoretical mathematical definition of parallel as it is unlikely that any process performed during surgery will be infinitely precise in the ability to put a line in a particular plane and make it parallel for an infinite extension of the lines in question. In order to achieve perfection, every aspect of the manufacturing process for the alignment jig would need to have infinite precision as would each step performed by the surgeon. Same is true for co-linear. Thus, the concepts of parallel and co-linear are meant to include situations that deviate from this theoretical ideal but do so in a way that makes the clinical results indistinct from the results that would have been obtained if the theoretical absolutes had been achieved.

The terms distal and proximal vary from field to field depending on the point of reference. In this disclosure and the claims that follow, proximal is defined in connection with the user holding the device in its typical orientation. Thus for a claw hammer, the hammer head and claw would be distal and the hammer handle would be proximal as the user typically holds the hammer by the handle. As the user will handle various portions of the alignment jig, it is perhaps easier to think of proximal and distal with respect to the cross bar (discussed below) so that the portions of the device closest to (or inside) the patient would be distal and the portions of the device closest to the cross bar would be proximal.

Figure 2:
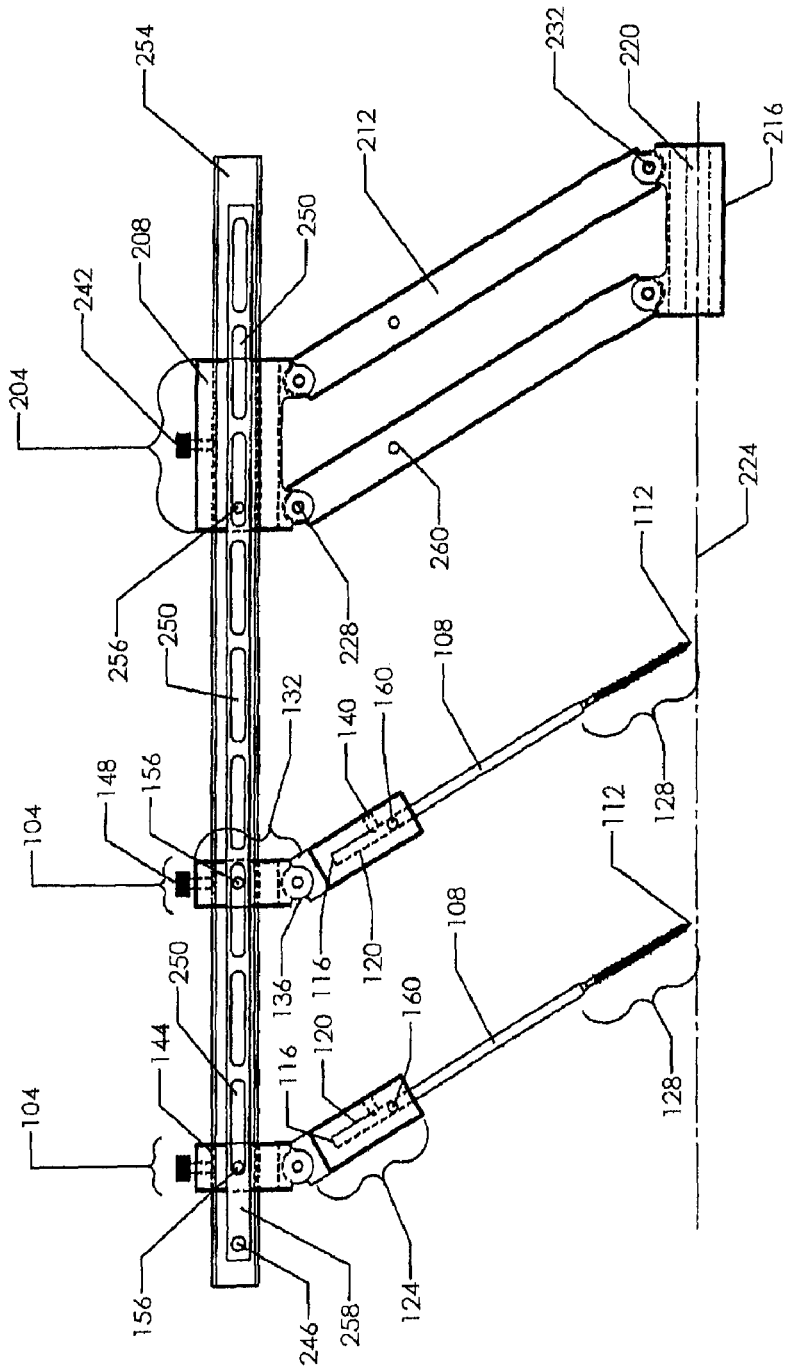
FIG. 2 is a side view sets forth the components found in one apparatus that may be used in an implementation of the present disclosure.
Figure 3:
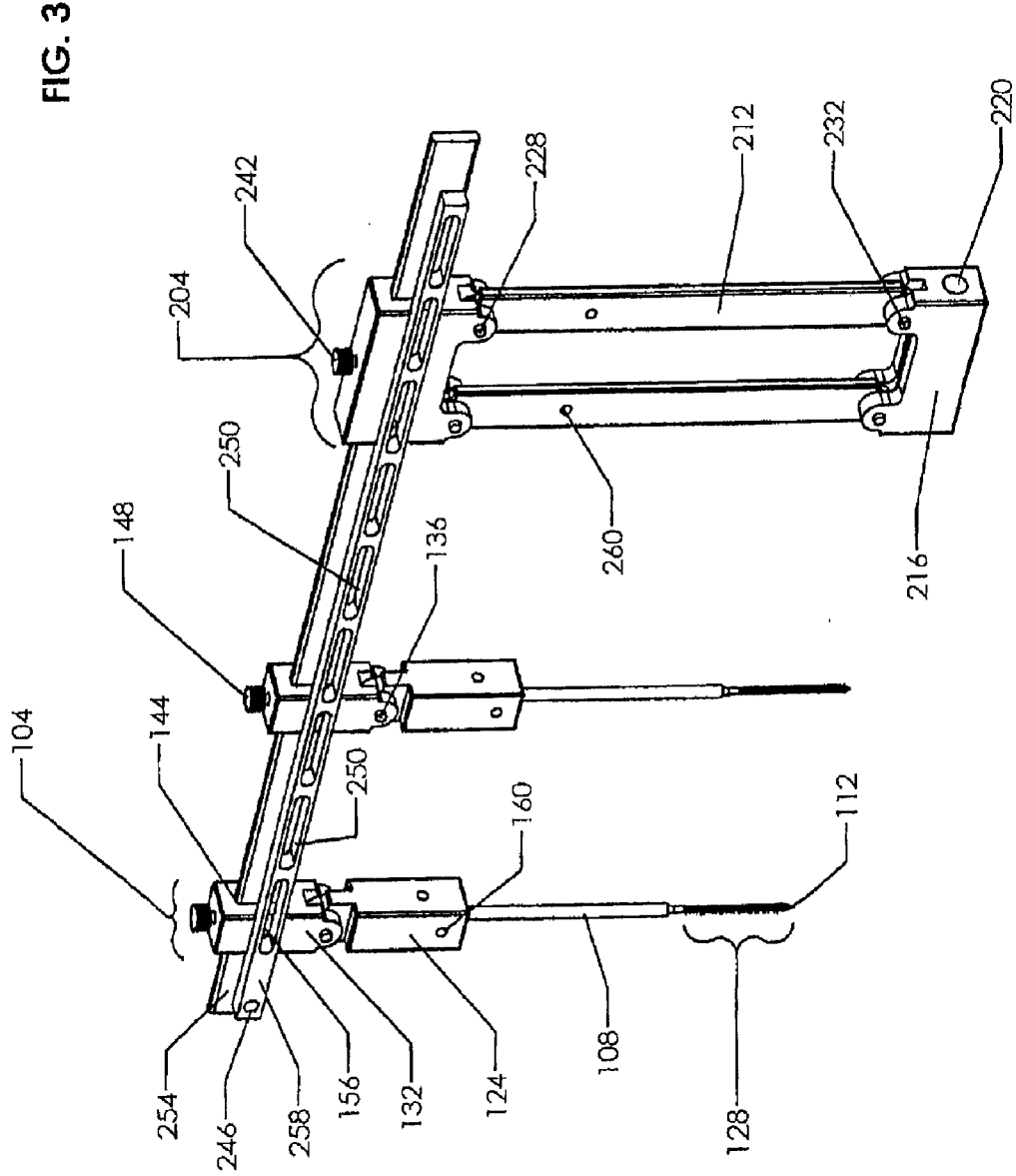
FIG. 3 is a top perspective view of an apparatus that may be used in an implementation of the present disclosure.

FIG. 2 is a side view sets forth the components found in one apparatus that may be used in an implementation of the present invention. The relationship between some components is easier to discern by looking a perspective view. FIG. 3 is a top perspective view of an apparatus that may be used in an implementation of the present invention. FIG. 2 shows an alignment jig 100 with a pair of swivel guide pin sheath assemblies 104 (and 105) with engaged guide pins 108, a swivel cannula guide assembly 204, a cross bar 254, a spacer bar 258 with slots 250 and stud assemblies 280 (not shown here but discussed below, and shown in FIG. 15).

Details Regarding Swivel Guide Pin Sheath Assembly

Each swivel guide pin sheath assembly 104 shown in FIG. 2 and FIG. 3 in engaged with a guide pin 108 with a guide pin tip 112. The guide pin 108 has a second end 116, away from the guide pin tip 112 which may be placed into an appropriate bore 120 in the lower portion 124 of swivel guide pin sheath assembly 104. The guide pins 108 may include a threaded portion 128 for engagement with material within a patient's body such as bone that forms part of a vertebra.

The lower portion 124 of the swivel guide pin sheath assembly 104 is hingedly connected to an upper portion 132 of the swivel guide pin sheath assembly 104 via a hinge element 136. These components are sometimes referenced by the names pin engager (in lieu of lower portion) and slider (in lieu of upper portion).

In the implementation shown in FIGS. 2 and 3, the guide pins 108, the bores 120, and the lower portions 124 are the same in each of the two swivel guide pin assemblies 104 so that the guide pin tips 112 are both the same distance away from the rotation point within the hinge element 136 for the respective swivel guide pin assembly 104. The guide pins 108 may be Kirschner wires sometimes referred to as "K-wires". In many implementations, the guide pins 108 will be identical including the length of the guide pins 104 and the alignment jig will be constructed so as to seat the guide pins 108 so that the guide pin tips 112 are both the same distance from the rotation point within hinge element 136 for the respective swivel guide pin assemblies 104. Alternatively, proper selection of guide pin length and bore depth may be used so that a pair of guide pins that do not have the same length could be seated in appropriately adapted bores so that the guide pin tips 112 are both the same distance from the rotation point within hinge element 136 for the respective swivel guide pin assemblies 104.

A retainer (not shown here) may be inserted into retainer bore 140 located in the lower portion and substantially orthogonal to bore 120, such as by threaded engagement, to retain the guide pin 108 so it is seated up against the end of the bore 140 in the lower portion so that the position of the guide pin tip 112 from the center of rotation point of the hinge element 136 does not vary after the retainer is inserted. One of skill in the art will recognize that the guide pin 108 could alternatively be retained by a press fit, or by clamps, latches, ratchet mechanisms, or other mechanisms known in the art for the selective retention of a component.

Figure 4:
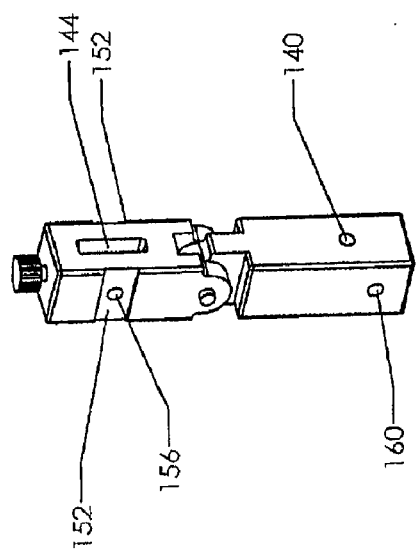
FIG. 4 is a perspective view of one implementation of a swivel guide pin sheath (sub?) assembly 104 without a guide pin 108.
Figure 5:
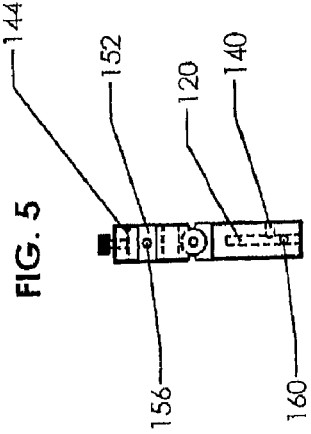
FIG. 5 is a front view of the same swivel guide pin sheath assembly 104 without a guide pin 108.
Figure 6:
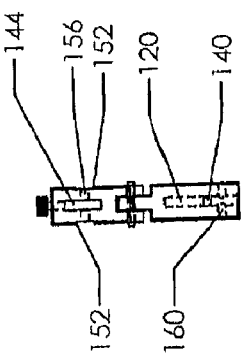
FIG. 6 is a side view of the same swivel guide pin sheath assembly 104 without a guide pin 108.

The upper portion 132 of the swivel guide pin sheath assembly 104 may contain a channel 144 which may be an interior cavity that runs through the upper portion 132. A thumbscrew 148 may be used to selectively affix the upper portion 132 to the cross bar 254 so that the upper portion 132 may not move relative to the cross bar 254. FIG. 4 is a perspective view of one implementation of a swivel guide pin sheath assembly 104 without a guide pin 108. FIG. 5 is a front view of the same swivel guide pin sheath assembly 104 without a guide pin 108. FIG. 6 is a side view of the same swivel guide pin sheath assembly 104 without a guide pin.

Channel 144 is visible in FIGS. 4-6. Retainer bore 140 is also visible in FIGS. 4-6 as the perspective view is from a side that shows the retainer bore 140. Looking at FIGS. 4-6, this implantation of the upper portion 132 of the swivel guide pin sheath assembly 104 has a pair of spacer bar channels 152.

Visible in FIGS. 2-6, the swivel guide pin sheath assembly 104 has an upper spacing landmark 156 and a lower spacing landmark 160. In these figures. the spacing landmarks are bores into the swivel guide pin sheath assembly 104. As discussed below, the spacing landmarks could be protrusions, or other landmarks.

Details Regarding the Swivel Cannula Guide Assembly

Details regarding swivel cannula guide assembly 204 may be seen in FIGS. 2 and 3 introduced above and in FIGS. 7-9 where FIG. 7 is a perspective view of a swivel cannula guide assembly 204, FIG. 8 is a side view of a swivel cannula guide assembly 204, and FIG. 9 is a front view of a swivel cannula guide assembly 204. The swivel cannula guide assembly 204 includes a slider 208, pair of extension bars 212, and guide block 216. The guide block 216 has a guide block cannula 220 and the guide block cannula 220 has a cannula centerline 224. As described in more detail below, the alignment jig 100 may be used to align the cannula centerline 224 relative to the guide pin tips 112 which are placed into a body to define an internal target path 20 (FIG. 1) so as to align delivery of therapy with the internal target path 20.

Each of the two extension bars 212 is hingedly connected to the slider 208 by an upper hinge element 228. Each of the two extension bars 212 is hingedly connected to the guide block 216 by a lower hinge element 232. When the swivel cannula guide assembly 204 has the cross bar 254 extending through a channel 236 in the slider 208, the hinge element configuration in the swivel cannula guide assembly 204 allows the guide block 216 with the guide block cannula 220 to translate in along the long axis of the cross bar 254. As the guide block 216 translates along the long axis of the cross bar 254 the distance between the guide block 216 and the cross bar will change with the maximum distance as the extension bars 212 are oriented perpendicular to the long axis of the cross bar 254. One aspect of the motion of the guide block 216 is the cannula centerline 224 remains parallel to the long axis of the cross bar 254 throughout the range of motion of the guide block 216.

The slider 208 may move along the long axis of the cross bar 254 until it is selectively affixed to the cross bar 254 by thumbscrew 242. As visible in FIGS. 7-9, the slider 208 may include a spacer bar channel 252. Most implementations with a spacer bar channel 152 in the swivel guide pin sheath assembly 104 are likely to have a corresponding spacer bar channel 252 in the swivel cannula guide assembly 204.

Like the swivel guide pin sheath assembly 104, the swivel cannula guide assembly 204 has an upper spacing landmark 256 and a lower spacing landmark 260. As it may be desirable to minimize the number of distinct parts, both extension bars 212 could be identical and thus both have a lower spacing landmark 260 even if one of the lower spacing landmarks is not used in a particular method of using the alignment jig 100 (method discussed below).

Parallelograms

The present invention makes use of the properties of parallelograms so it is useful to review the properties of these quadrilaterals. In FIG. 10, parallelogram 300 has two pairs of parallel lines. Lines 304 and 308 are parallel and of equal length. Lines 312 and 316 are parallel and of equal length.

First Parallelogram.

FIG. 11 shows a first parallelogram 320. The sequence of actions needed to from this parallelogram will be described below but it is useful to see the parallelogram before getting into that detail. When the distance (A) of line 324 between the lower spacing landmarks 160 on the two swivel guide pin sheath assemblies 104 is replicated on the line 328 between the upper spacing landmarks 156 so that they are also spaced at distance (A) and affixed to crossbar 254 to maintain that distance (A), line 332 between the centerlines of the two hinge elements 136 which are both offset a fixed distance (B) from the cross bar 254 is also a distance (A) (lines 336 and 340). The distance between the centerline of the hinge element 136 and the lower spacing landmark 160 is a distance (D) and is the same in each of the two swivel guide pin sheath assemblies 104 (lines 344 and 348).

Thus, parallelogram 320 has a pair of opposite sides 324 and 332 that are the same length (A), and has a second set of sides 336 and 342 which are the same length (D). As a quadrilateral with a pair of opposite lines of the same length as each other and a second pair of opposite lines that are the same length as each other must be a parallelogram, then lines 344 and 348 must be parallel to one another and line 324 must be parallel to line 332.

This exercise in geometry is interesting as it means that the internal target path 360 defined by the two guide pin tips 112 is now parallel to lines 324, 332, and 328. This is known to be true as the extension 356 of line 344 is parallel to the extension 352 of line 348 as they are extensions of parallel lines. As the length of the guide pin 108 from the lower spacing landmark 160 to the guide pin tip 112 is going to be the same in each of the two swivel guide pin sheath assemblies 104 as the guide pins 108 are the same length in each case and the second end 116 of each guide pin 108 is placed against the end of the bore 120 in the lower portion 124 of the swivel guide pin sheath assembly 104. With two opposite sides 352 and 356 of the same length and parallel, segment 364 of internal target path 360 (which is not visible to the user as the guide pin tips 112 are inserted into the body and are thus below the body surface 196) must be parallel to line 324 and thus parallel to lines 332 and 328.

After creating parallelogram 320, the upper spacing landmarks 156 are now parallel to the guide pin tips 112. As the upper spacing landmarks 156 are part of the upper portions 132 and the upper portions 132 have the cross bar 256 connecting the upper portions 132, the creation of first parallelogram 320 has placed cross bar 256 parallel with the internal target path 360 as defined by the two guide pin tips 112.

Second Parallelogram.

Figure 12:
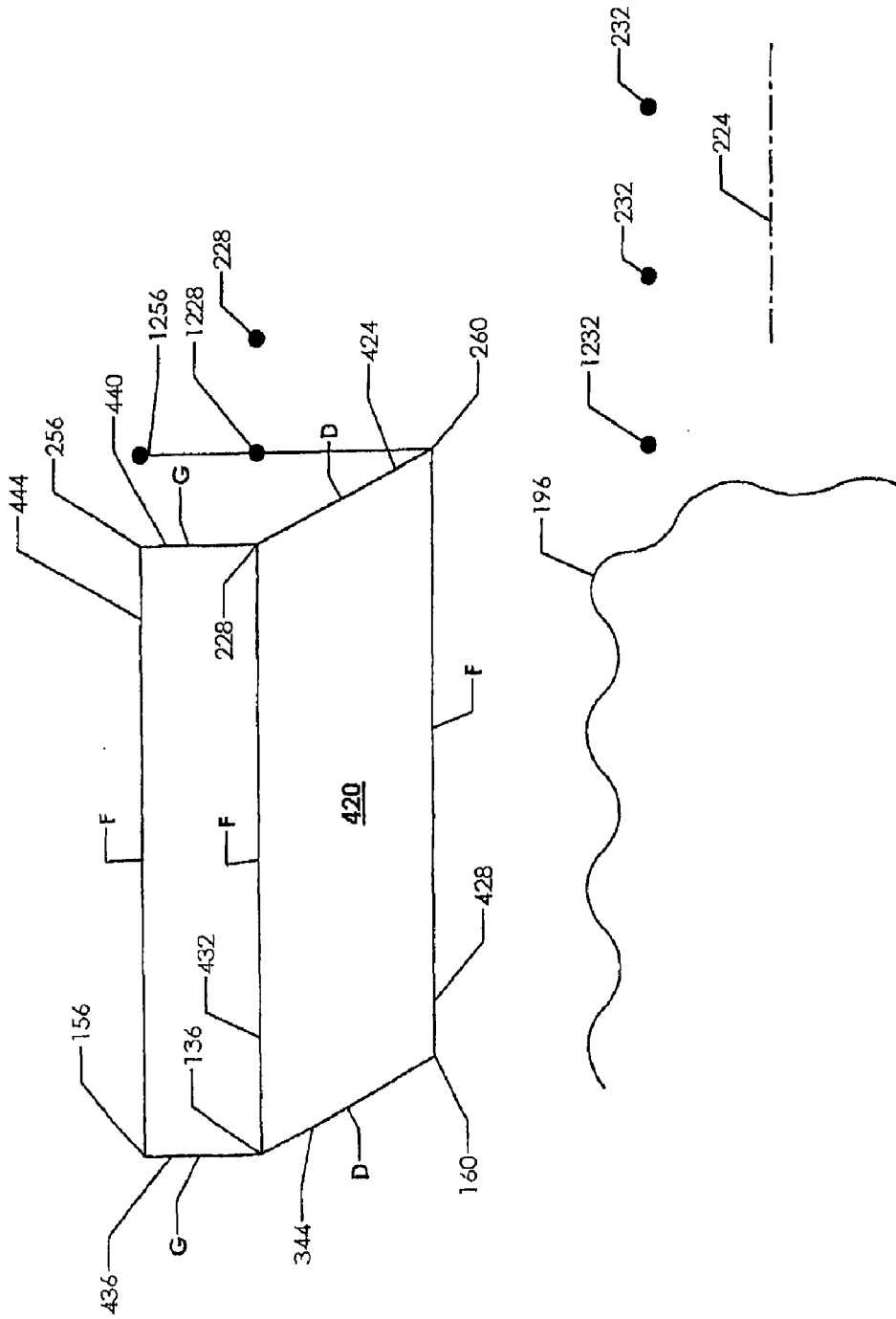
FIG. 12 shows a second parallelogram 420 created while using an alignment jig.

FIG. 12 illustrates the second parallelogram 420. As in FIG. 11, FIG. 12 shows reference points from FIGS. 2 and 3 as they apply to the context of the second parallelogram 420. Line 344 between the center of rotation of hinge element 136 and lower spacing landmark 160 has a length of D. Line 344 was part of the first parallelogram 320. As an aside, the present invention could be implemented by using a different lower spacing landmark for the first parallelogram 320 than is used in the second parallelogram 420 as long as this was compensated for in other spacing landmarks so line 344 does not need to be in common between the two parallelograms.

Line 424 between the center of rotation of one of the upper hinge elements 228 on the swivel cannula guide assembly 204 and the lower spacing landmark 260 may be set to be the same length D as the length of line 344. In this implementation, the extension bar 212 on the left side of the swivel cannula guide assembly 204 is used in the second parallelogram 420. After reading this disclosure, one or ordinary skill in the art will appreciate that the right extension bar and related reference points could be used as part of the second parallelogram 420.

If the swivel cannula guide assembly 204 (FIG. 2) starts with the extension bars 212 substantially perpendicular to the cross bar 254 and the channel 236 in slider 208 contains a portion of the cross bar 254, then the initial position of the centerline of the upper hinge element 228 would be as shown at point 1228 and the initial position of the upper spacing landmark 256 would be at point 1256. Note that the position of the guide block cannula (not shown in FIG. 12) would be outside of the patient's body 196 as indicated by the centers of rotation of the leftmost of the two lower hinge elements 232 shown at initial point 1232

One way to get line 424 parallel to line 344 is to set lines 428 and 432 to be the same length ("F") as that would form a quadrilateral with a pair of opposite lines of length D and the other pair of opposite lines of length F. If both pairs of lines have common lengths, then it is a parallelogram. The distance between the lower spacing landmark 160 and the lower spacing landmark 260 may be replicated by moving the slider 208 along the cross bar 254 so that the distance between upper spacing landmark 156 and upper spacing landmark 256 (line 444) becomes distance F. The slider may be selectively affixed to the cross bar 254 to prevent additional movement of the slider 208 by tightening slider thumbscrew 242.

As the distance on line 436 between the upper spacing landmark 156 and the center of rotation of the hinge element 136 may be created to be length G and the distance on line 440 between upper spacing landmark 256 and the center of rotation of the nearby upper hinge element 228 may be manufactured to also be length G. The lines 436 and 440 may be manufactured to be parallel to one another (most likely by being perpendicular to the long axis of the cross bar 254). Lines 444 and 432 may be manufactured to be parallel to one another. Thus, the lines 436, 444, 440 and 432 form a parallelogram (most likely a rectangle) such that lines 444 and 432 have the same length and setting line 444 to length F sets line 432 to length F.

Now that the pair of lines 344 and 424 have the same length and pair of line 432 and 428 have the same length, quadrilateral 420 is a parallelogram. The relevance of parallelogram 420 may be better understood through FIG. 13.

Figure 13:
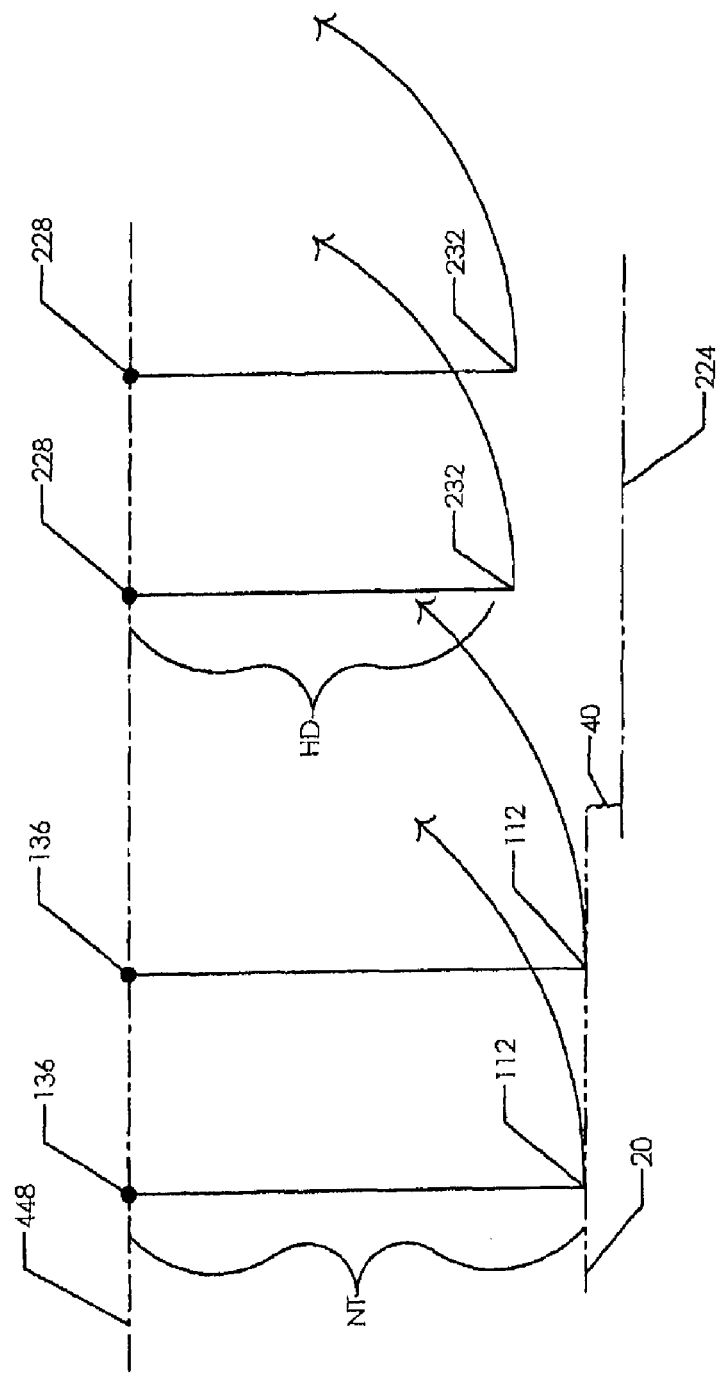
FIG. 13 represents the components that are free to rotate around the hinge elements 136 and upper hinge elements 228.

FIG. 13 represents the components that are free to rotate around the hinge elements 136 and upper hinge elements 228. As the guide pin tips 112 rotate a uniform amount around the center of rotation in the hinge elements 136, the internal target path 20 moves relative to the pair of upper hinge elements 136 while remaining parallel to the line 448 running through the hinge elements 136. Likewise the uniform rotation of the centerline of rotation of the lower hinge elements 232 relative to the centerlines of the pair of upper hinge elements 228 raises the guide block 216 (not shown in FIG. 13) containing cannula centerline 224 while keeping centerline 224 parallel to the centerlines of the upper hinge elements 228.

If the guide pin tips 112 are rotated an angle alpha (not shown) and through the use of the parallelograms, the alignment jig 100 (FIG. 2) ensures that the swivel cannula guide assembly 204 (not shown in FIG. 13) is rotated the same angle alpha so that lines 344 and 424 in FIG. 12 are parallel, then the movement of the internal target path 20 towards the line 448 running through the centerlines of hinge elements 136 and 228 will be similar in magnitude to the movement of cannula centerline 224 so that the amount of offset 40 between the internal target path 20 and the cannula centerline 224 will stay substantially similar for a range of angles, alpha.

As the distance between 136 and 112 in FIG. 13 (distance NT) is longer than the distance between 228 and 232 in FIG. 13 (distance HD), the rate of change in position of internal target path 20 as a function of the change in alpha will not be identical to the rate of change of cannula centerline 224 as a function of the change in alpha.

To the extent that an implementation wanted to maintain offset 40 (especially if offset 40 was desired to be zero so that the internal target path 20 and cannula centerline 224 are desired to be co-linear) then one of ordinary skill in the art would move the center of rotation of the lower hinge elements 232 downward and outside of the guide block so that the distance HD equals NT. To maintain a fixed offset in an implementation where distance NT equals distance HD, the cannula can be moved in the guide block relative to lower hinge elements 232 in order to provide any desired offset. (The offset could be in the plane containing line 448 and the internal target path 20 or in a plane perpendicular to that plane or both.)

Figure 14:
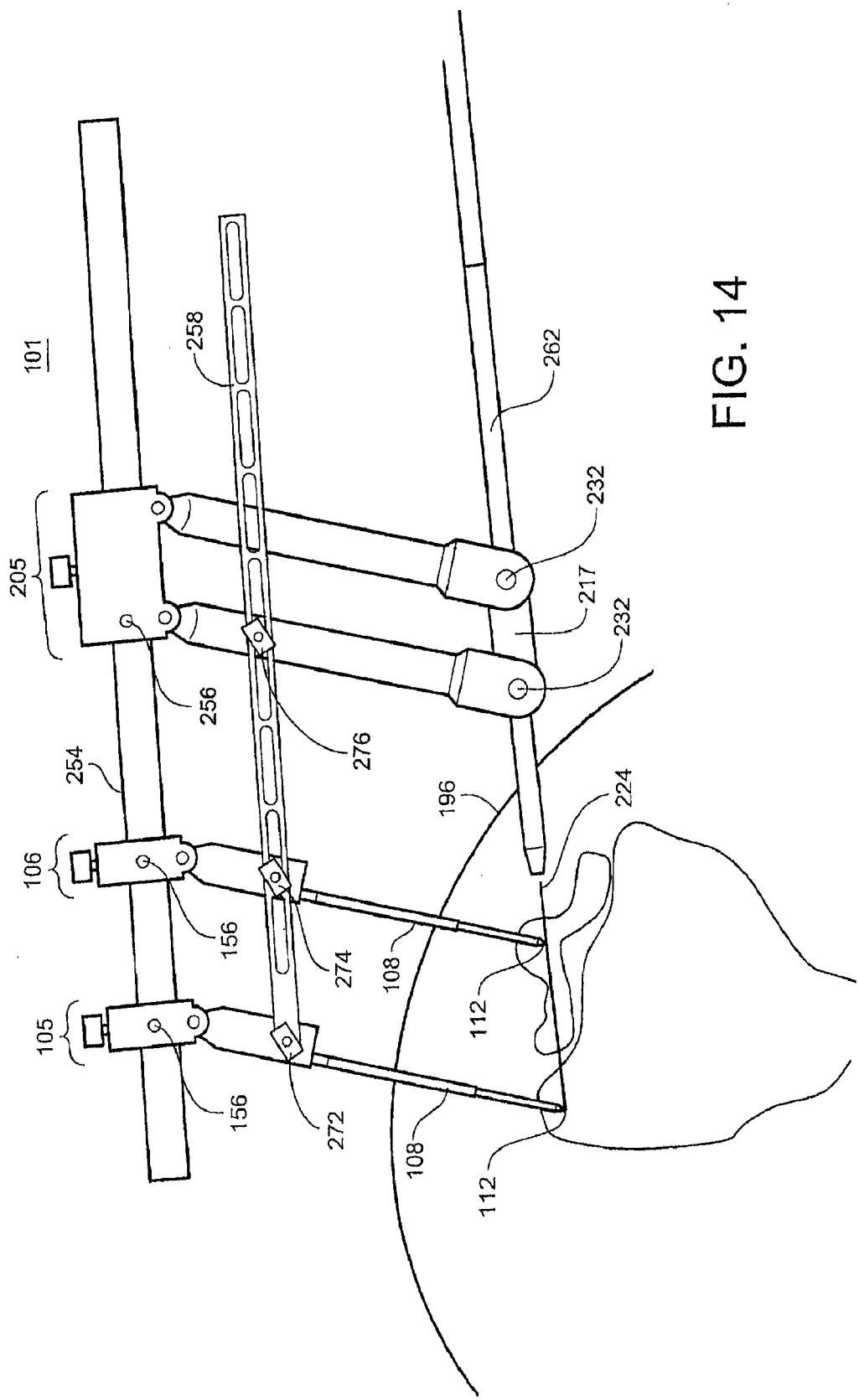
FIG. 14 shows an implementation of an alignment jig 101 with swivel guide pin sheath assemblies 105 and 106 and swivel cannula guide assembly 205.

FIG. 14 shows an implementation of an alignment jig 101 with swivel guide pin sheath assemblies 105 and 106 and swivel cannula guide assembly 205. Spacer bar 258 is being used in the process of establishing the second parallelogram. Note that FIG. 14 has stud assemblies 272, 274, and 276 at three places on the spacer bar 258 to highlight that either of the two swivel guide sheath assemblies 105 or 106 could be used to form the second parallelogram with swivel cannula guide assembly 205. Optionally, all three stud assemblies 272, 274, and 276 could be used in the process of creating the second parallelogram in order to provide assurance that the guide pins 108 remain parallel to one another. The centerlines of the lower hinge elements 232 are set lower relative to the guide block 217 than the alignment jig 100 described above such that the cannula centerline 224 may be kept co-linear with the pin tips 112 over a range of angles. FIG. 14 includes a working cannula 262 that is aligned by the guide block cannula (not visible here) in the guide block 217.

Replicating Distances.

FIG. 15 contains several views of a stud assembly 280. The stud assembly 280 includes a threaded stud 284 which may be passed through an opening in the spacer bar 254 before the thumbscrew head 294 is threadedly engaged with the threaded portion 288 of the threaded stud 284. As the thumbscrew head 294 is threadedly advanced against the spacer bar 254, the bar engagement section 290 of the threaded stud 284 engages with the spacer bar 254 and additional tightening of the thumbscrew head 294 affixes the position of the stud assembly 280 on the spacer bar 254. Before the stud assembly 280 is tightened, the stud assembly 280 may move relative to the spacer bar 258 by moving in one of the slots 250. If the stud assembly 280 is engaged with hole 246, then that stud assembly 280 may not move relative to the spacer bar 258. Protrusion 292 is intended for insertion into a similarly shaped cavity when cavities are used for the various spacing landmarks (156, 256, 160, and 260). One of skill in the art will recognize that divider calipers (sometimes simply "dividers") could be used to engage with spacing landmark cavities to capture and replicate a distance and these mechanisms are designed to hold a measured distance. Divider calipers could be used in conjunction with spacing landmarks that are visual indicia such as cross hairs (not shown) although the positive engagement between the tips of the caliper divider and a cavity type spacing landmark, may be desirable in a surgical setting where visual indicia may be difficult to see. While it might be awkward and difficult to do with precision, someone may implement an alignment jig without a spacer bar or a caliper divider and simply use a measuring implement such as a ruler to discern the distance between distance landmarks and to replicate that distance between another pair of distance landmarks. Such an implementation would lack the benefit of alignment jig rigidity that comes from having a spacer bar positively engaged with spacing landmarks.

One of skill in the art will appreciate that spacing landmarks could be implemented as protrusions with cavities in the landmark engagement section of stud assemblies (this variation not shown).

One of skill in the art will recognize that some alignment jigs may be implemented with extension bars that have the portion of the extension bar with the lower spacing landmark 260 built up so that the opening to the lower spacing landmark 260 is in the same plane as the lower spacing landmarks 160 in the swivel guide pin sheath assembly 104. Alternatively, a spacer bar channel analogous to element 154 could be added to recess the lower spacing landmarks 160 in the swivel guide pin sheath assembly 104 (or some combination of both).

The teachings of the present invention may be used in any situation where guide pin tips may be reliably placed to identify an internal target path for a desired therapy (such as application of a fixation screw). Once the internal target path is identified through use of guide pins that are placed somewhat parallel to one another as they pass from outside of the body to the target path, an alignment jig implementing various teachings from the present disclosure may be used to align the delivery of therapy to be either co-linear with the internal target path or nearly co-linear with the internal target path including parallel with an intentional offset.

Method Steps.

Figure 16:
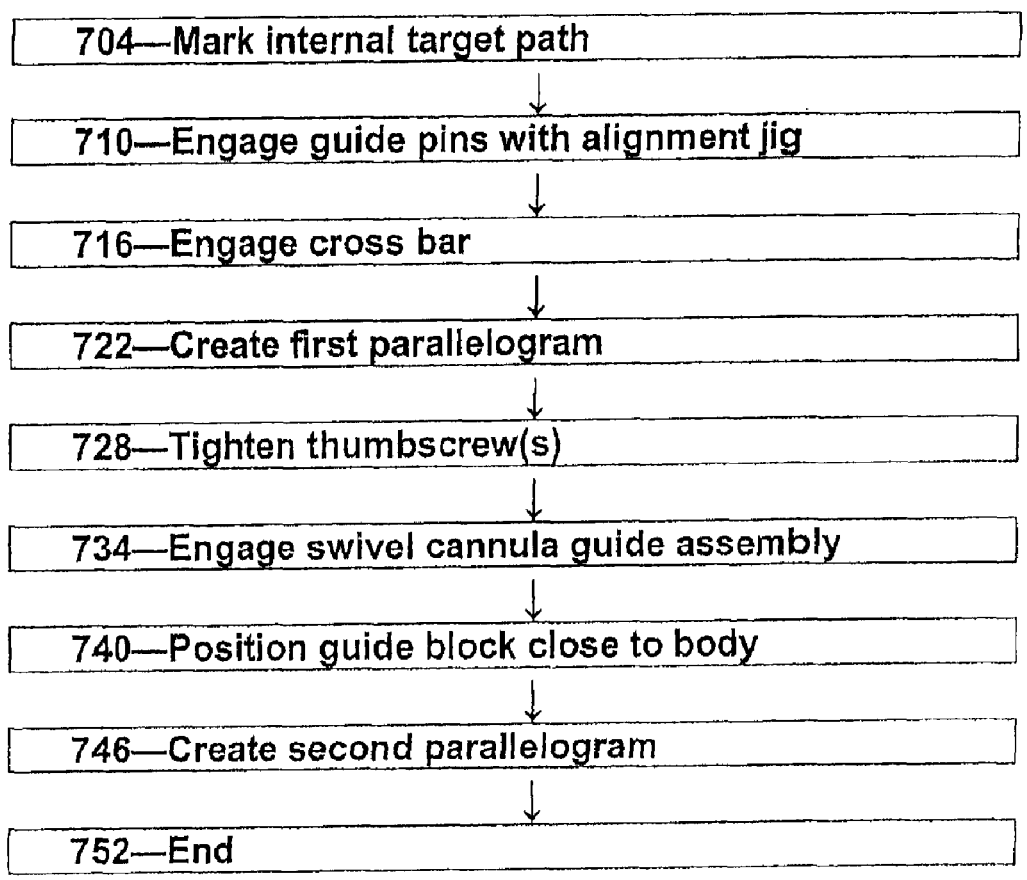
FIG. 16 is a flow chart of a process of using an alignment jig.

As a way of summarizing the information provided above, one set of steps for using an alignment jig are set forth below and reflected in FIG. 16. One of skill in the art will recognize that in some cases that the order of these steps may be changed without departing from the teachings of this disclosure.

504—place the pair of guide pins into the body to mark the internal target path with the guide pin tips. Some implementations, particularly those involving placement of guide pins tips into bone, may benefit from having a threaded portion of the guide pin to help maintain the precise position of the guide pin during the use of the alignment jig.

510—Engage the guide pins in the lower portion of the swivel guide pin sheath assembly (sometimes this lower portion is called the pin engager). The back of the guide pin should be inserted until seated or otherwise positioned in such a way to provide a predictable distance to the pin tip from the center of rotation of the hinge element in the swivel guide pin sheath assembly. After positioning each of the guide pins, selectively affix each of the guide pins to the lower portion of the swivel guide pin assembly so that the position of the guide pin relative to the respective swivel guide pin assembly remains constant.

516—Engage the upper portions of the swivel guide pin sheath assemblies with the cross bar. The implementation shown above use a rectangular cross bar and corresponding internal cavities in the upper portions of the swivel guide. The cross bar could be any uniform cross section (so elements can slide along the cross bar). The cross bar could be cylindrical, the shape of an I-beam, or some other shape of choice. The cross bar does not have to be inserted through an internal cavity, but could use a channel that is open on one side, or some other form of engagement with the upper portion of the swivel guide pin sheath assembly.

While some may create an implementation that has a swivel guide pin sheath assembly that is permanently affixed to a cross bar as the relative movement of one swivel guide pin sheath assembly to another could be achieved with only one swivel guide pin sheath assembly being capable of movement prior to being selectively affixed, other implementations will choose to use identical swivel guide pin sheath assemblies and engage both with the cross bar.

522—Create the First parallelogram by capturing the distance between lower spacing landmarks on the swivel guide pin sheath assemblies and adjusting the relative distance between the upper portions of the swivel guide pin sheath assemblies to achieve that particular spacing between the upper spacing landmarks on the swivel guide pin sheath assembly.

528—Tighten Thumbscrew(s) so that neither of the swivel guide pin assemblies can move along the cross bar.

534—Engage the Swivel Cannula Guide Assembly with the cross bar but leave it free to slide along the cross bar.

540—Move the Swivel Cannula Guide Assembly so that the Guide Block is close the surface of the patient's body, perhaps even to the point of being snug against the patient's skin.

546—Create the Second Parallelogram. Capture the distance between the lower spacing landmark on one of the two swivel guide pin sheath assemblies and the lower landmark on the extension bar near an upper landmark (note if there is an upper landmark above both extension bars, then either one could be used). Move the slider 208 along the cross bar to obtain the same distance as the captured distance so that the distance between an upper landmark on a swivel guide pin sheath assembly and an upper landmark on the swivel cannula guide assembly is the same as the distance between the corresponding lower landmarks. One of skill in the art will recognize that if the alignment jig is positioned so as to be roughly in the correct alignment (including having the swivel cannula guide assembly 204 roughly parallel with the relevant portions of the swivel guide sheath assemblies 104, that one could capture the distance between the upper spacing landmark on one of the two swivel guide pin sheath assemblies and the upper landmark on the swivel guide cannula assembly and then replicate that distance on the appropriate lower landmarks.

552—End. The guide block cannula centerline is now aligned with the internal target path. Aligned includes co-linear and parallel with an offset from co-linear. Depending on the specific geometry of the alignment jig, a portion of the offset may be attributed to a function of the angle of the guide pins relative to the cross bar.

Use of the Alignment Jig to Provide Therapy to Facet Joints.

The spinal column is a complex system of bone segments (vertebral bodies and other bone segments) which are in most cases separated from one another by discs in the intervertebral spaces (sacral vertebrae are an exception). In the context of the present disclosure, a "motion segment" includes adjacent vertebrae, i.e. an inferior and a superior vertebral body, and the intervertebral disc space separating said two vertebral bodies. Unless previously fused, each motion segment contributes to the overall flexibility of the spine contributes to the overall ability of the spine to flex to provide support for the movement of the trunk and head.

The individual motion segments within the spinal columns allow movement within constrained limits and provide protection for the spinal cord. The discs are important to cushion and distribute the large forces that pass through the spinal column as a person walks, bends, lifts, or otherwise moves. Unfortunately, for a number of reasons, for some people, one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

It has been estimated that in 2004 there were over 700,000 surgical procedures performed annually to treat lower back pain in the U.S. It is conservatively estimated that in 2004 there were more than 200,000 lumbar fusions performed in the U.S. and more than 300,000 worldwide, representing approximately a $1 B endeavor in an attempt to alleviate patients' pain. Approximately 60% of spinal surgery takes place in the lumbar spine, and of that portion approximately 80% involves the lower lumbar vertebrae designated as the fourth lumbar vertebra ("L4"), the fifth lumbar vertebra ("L5"), and the first sacral vertebra ("S1"). Persistent low back pain is often attributable to degeneration of the disc between L5 and S1.

A range of therapies have been developed to alleviate the pain associated with disc problems. One class of solutions is to remove the failed disc and then fuse the two adjacent vertebral bodies together with a permanent but inflexible spacing, also referred to as static stabilization. As mentioned above, an estimated 300,000 fusion operations take place each year. Fusing one section together ends the ability to flex in that motion segment. While the loss of the normal physiologic disc function for a motion segment through fusion of a motion segment may be better than continuing to suffer from the pain, it would be better to alleviate the pain and yet retain all or much of the normal performance of a healthy motion segment.

The facet joints, which are positioned between each pair of adjacent vertebrae, share and support with the respective intervertebral disc included in that motion segment, compressive axial loads on the spine. Thus, it is also known to place fixation devices such as screws, either directly across the facet joints of adjacent vertebrae or indirectly across the facet joints through the lamina (i.e. translaminar) as a primary mechanism for spinal fixation and also as an ancillary mechanism for fixation to augment anterior fusion or pedicle screw fixation instrumentation, and as such, both direct and translaminar facet screws are often being implanted.

One use of the alignment jig is to allow surgeons to accurately and reproducibly deploy, fixation devices such as translaminar facet screws across the facet joints to affix adjacent vertebrae in via a minimally invasive, percutaneous approach.

In order to convey details of a particular use of the alignment jig it is useful to explain some details of the relevant anatomy. Vertebrae differ from person to person and from top to bottom of the spinal column within a particular person. Thus, the size, shape, and angular projections of the protrusions (called processes) from the vertebrae vary considerably from these examples that are typical of the lumbar section of the spine. These views discussed below while not perfect representations of every vertebrae, are sufficient to introduce the various components of interest.

In the context of the present disclosure anterior refers to in front of the spinal column (ventral); posterior refers to behind the column (dorsal); cephalad means towards the patient's head (also sometimes "superior," or distal); caudal refers to the direction or location that is closer to the feet (also sometimes "inferior," or proximal).

While it is useful to see two adjacent vertebrae in their anatomic relationship to one another, it may be more useful to start with a view of a single vertebra.

Figure 17:
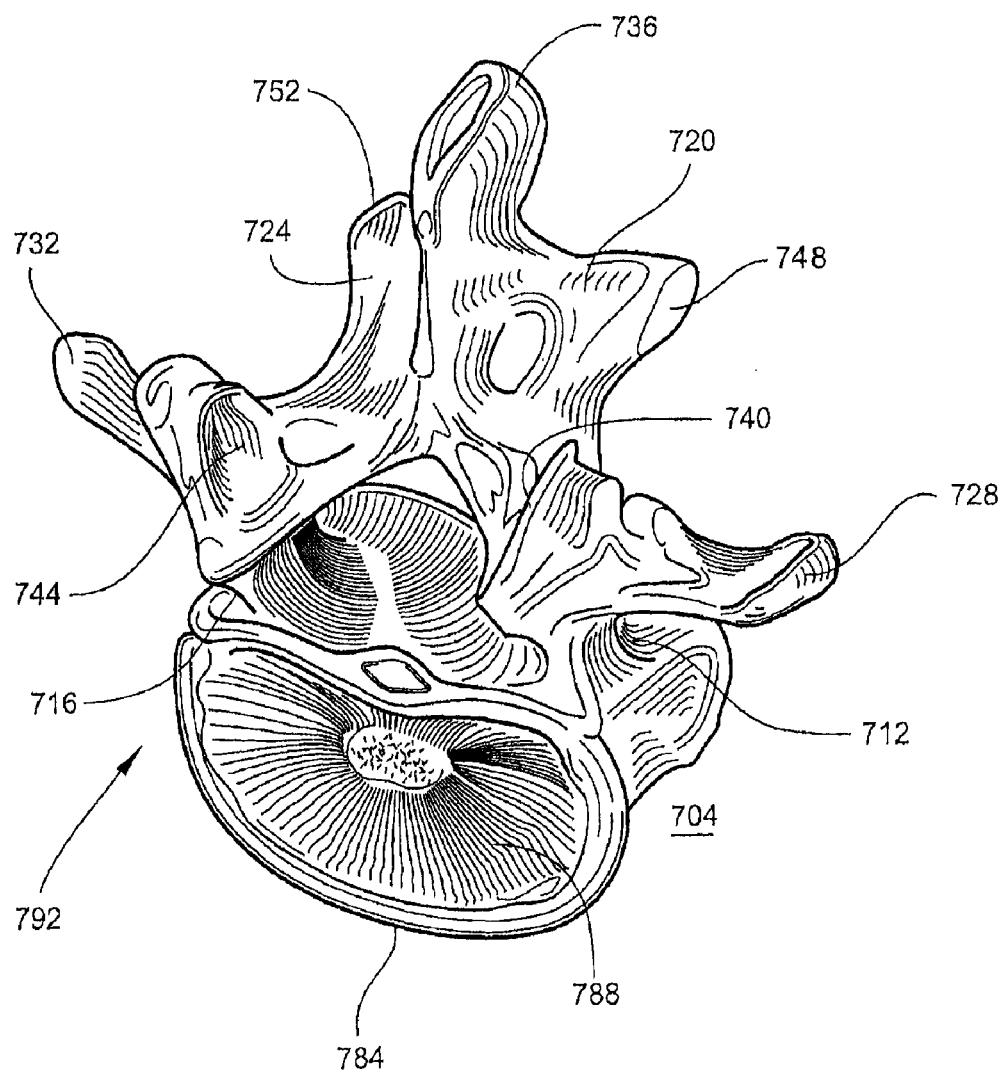
FIG. 17 is a top perspective view of a single vertebra 704.

FIG. 17 is a top perspective view of a single vertebra 704. The vertebra has a hard outer shell of cortical bone 784 and an interior of cancellous bone 788.

The spinal cord (not shown) is protected in the spinal foramen 792 formed by the two pedicles 712, 716 and the two laminae 720, 724. Extending from the pedicles are two transverse processes 728, 732. Extending from the midline of the vertebra where the two laminae meet is the spinous process 736. These three processes serve as connection points for ligaments and muscle.

Vertebrae move relative to one other in order to allow the spine to bend forward (flexion), bend backward (extension), bend to the right or left (lateral bending), twist (rotate in the z-axis) and other forms of movement. While the disc 780 plays an important part in this movement in absorbing shocks and distributing loads, there are also joints on the posterior side of the spinal column that allow for movement of a vertebra relative to an adjacent vertebra.

These joints are called facet joints. Most vertebrae have four facet joints. Two facet joints between a particular vertebra and the adjacent cephalad vertebra and two facet joints between the particular vertebra and the adjacent caudal vertebra.

The components of the facet joints are the superior articular process 740 and 744 and the inferior articular process 748 and 752.

Figure 18:
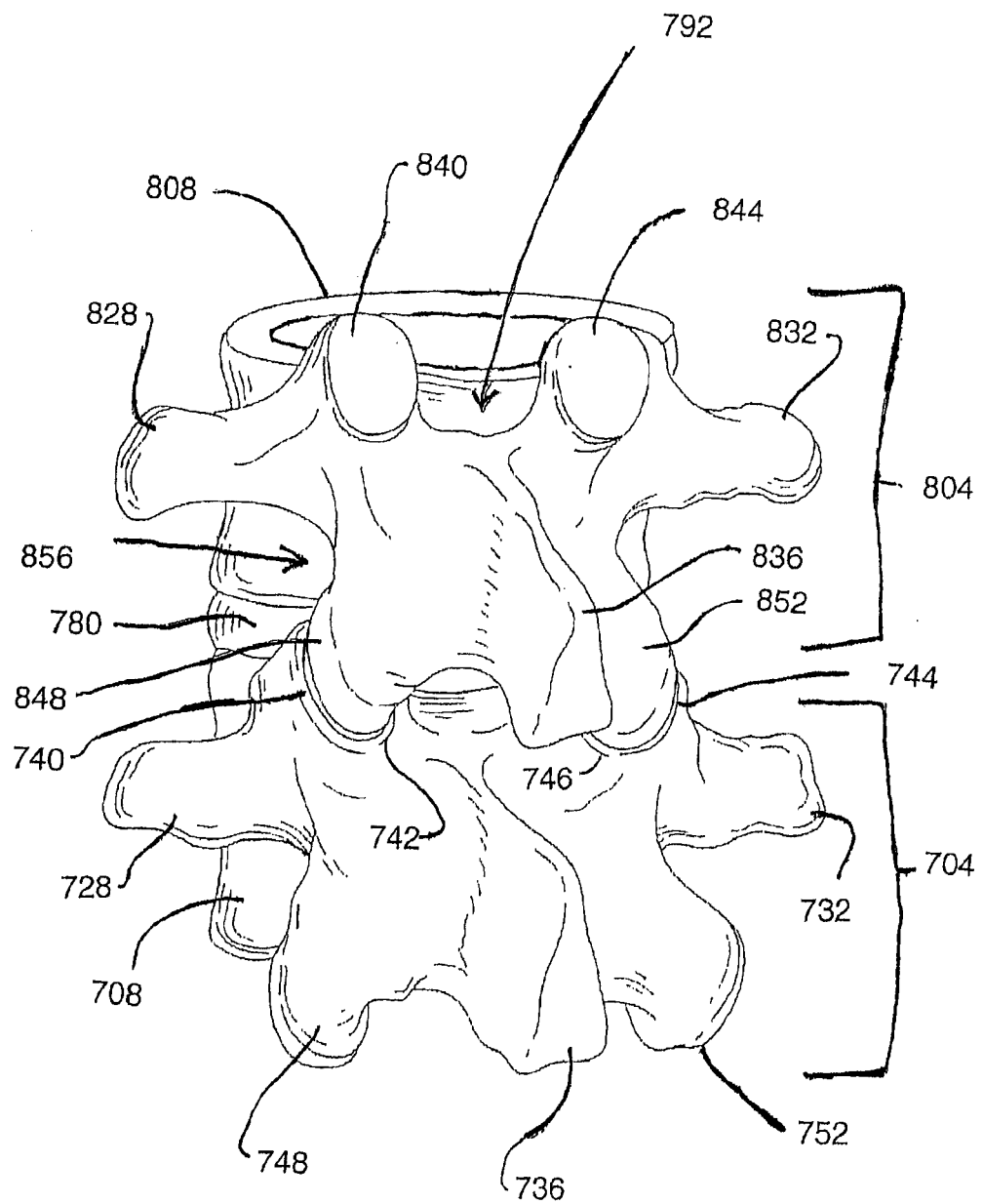
FIG. 18 is a rear perspective view of a motion segment 700 with a lower (more caudal) vertebra 704 and a higher (more cephalad) vertebra 804.

FIG. 18 is a rear perspective view of a motion segment 700 with a lower (more caudal) vertebra 704 and a higher (more cephalad) vertebra 804. The anterior portion of the vertebra is the vertebral body 708, 808. Between the two vertebral bodies 708 and 808 is a disc 780. The spinous processes 736 and 836 and the transverse processes 728, 732, 828, 832 are visible in this view.

The facet joint portion of the superior articular processes 740 and 744 for vertebra 704 are engaged by the inferior articular processes 848 and 852 of vertebra 804 to as part of facet joints 742 and 746. The superior articular processes 840, 844 for the vertebra 808 are visible as they would engage with the inferior articular processes from the next more cephalad vertebra. Likewise the inferior articular processes 748, 752 of vertebra 704 would engage with the superior articular processes of the next more caudal vertebra. A neuralforamen 856 (sometimes neural foramen) is partially visible in FIG. 18. There is another neuralforamen on the opposite side. The neuralforamina provide a passage for the nerves connecting to the spinal cord. If this passage way is constricted, the constriction called stenosis of the neuralforamina can cause pain or other neural symptoms.

One therapeutic treatment of the facet joint is to affix the superior articular process to the inferior articular process using a facet screw. Traditionally, this was accomplished using normal surgical techniques but there are consequences of gaining access to the area to receive therapy using traditional highly invasive surgical techniques.

Figure 19:
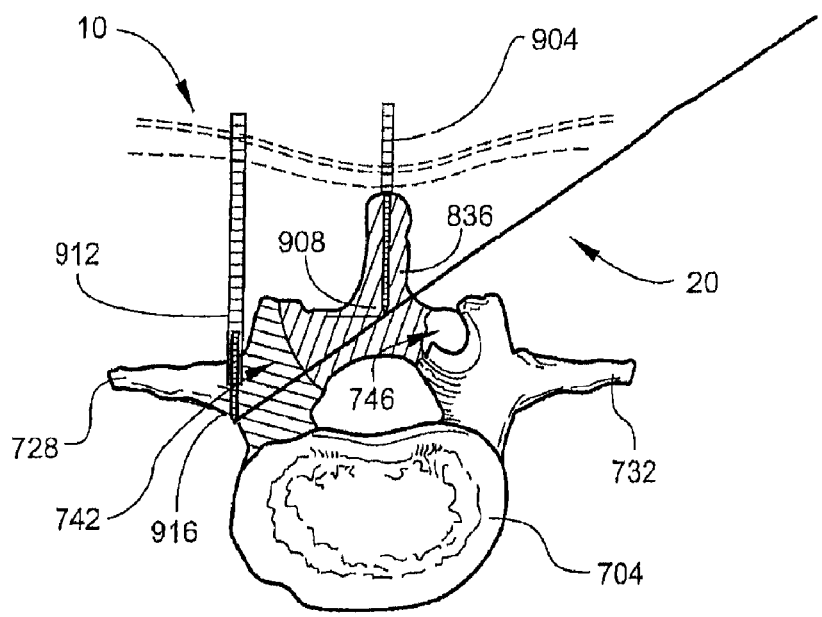
FIG. 19 is a cross-section view of the spine showing placement of guide pins 108 to define an internal target path 20 for delivery of a first translaminar facet screw.

To use an alignment jig in keeping with the present disclosure in a minimally invasive procedure, the patient is placed in the prone position and X-ray imaging equipment is set-up to provide views in both the anterio-posterior (AP) plane and the lateral plane so that the procedure can be performed under fluoroscopic guidance. It should be understood to those skilled in the art that other known navigation assistance devices and equipment could alternatively be used. A stab incision is then made through the skin of the patient body 10 and the first K-wire (guide pin 904) is inserted through the incision and into the center of the spinous process 836 of the more cephalad vertebra 804 (such as the L4 vertebra). (Note only the lower portion of guide pin 904 is shown in FIG. 19). The distal end (i.e. that farthest from the surgeon) of the first K-wire 904 is threaded or tapped into the spinous process 836 until the distal tip 908 reaches a point along the internal target path 20 on which a first screw is to be inserted.

Next, through another percutaneous stab incision into the patient's body 10, the second K-wire 912 is inserted into the transverse process 728 on a first side (the left side, viewed in FIG. 19) of the more caudal vertebra 704 such as the L5 vertebra and extends in parallel with the first K-wire 904 in both the sagittal and coronal planes. (Again, only the lower portion of K-wire 912 is visible in FIG. 19. The distal end 916 of the second K-wire 912 is threaded or tapped into the transverse process 728 just lateral to the facet joint 742 on the first side of the vertebra 704 up to the junction of the transverse process 728 and the pedicle on the first side.

The establishment of the internal target path 20 an important aspect of the delivery of therapy as the alignment jig 100 creates an external alignment line 30 based on the internal target path 20 but the alignment jig does not check the accuracy of the internal target path. Thus, the skill of the surgeon is important to establishing a suitable internal target path. The first guide pin (such as a K-wire) is inserted (often by "feel") by the surgeon into the center of the spinous process 836 of the upper vertebra 804 of two adjacent vertebra. The guide pins, and in particular the second pin placed into a transverse process (728 or 732), may be placed via assistance of fluoroscopic visualization. While not part of the apparatus for translating an internal target path from inside a patient's body to outside the patient's body, a guide pin stop (safety stop) may be used by a surgeon to limit the depth of insertion of the guide pin into the spinous process 836.

The initial placement of these guide pins by the surgeon through the patient's skin and into position in bone will determine the ultimate accuracy of the external alignment line used to align the deliver of the fixation device such as a screw. The depth of pin insertion into bone will vary according to patient anatomy, and may be between about 25 mm to 35 mm, often about 30 mm.

After the establishment of the internal target path 20, an alignment jig such as described above is then used to align an external path with the internal target path 20 so that therapy can be applied either co-linear with the internal target path 20 or with some offset. In FIG. 19, the therapy is apt to be applied from the right side and downward.

After the external alignment line 30 is established, the jig assembly 100 may be made more rigid by applying stud assemblies to all lower spacing landmarks (160 (both) and 260). This is an optional step and it is anticipated that many surgeons will not perform this step.

Once the path for application of therapy has been established outside of the body, a scalpel (not shown) may be used to incise the skin to accept the a working cannula (such as 262 in FIG. 14). The incision is made using the passage through the cannula guide of the assembly to orient the incision along the external alignment line (See FIG. 1 element 30). Under fluoroscopic guidance, a guide wire is passed through the incision along the extension of the external alignment line to the surface under fluoroscopic guidance. Next, a dilator and or dilator with sheath are passed over the guide wire to create subcutaneous space for the working cannula 282 along the external alignment line 30. The dilator and dilator sheath assembly are guided for movement along the external alignment line 30 by virtue of the passage through the guide block cannula 220, and are passed over the guide wire. These are moved along the external alignment line 30 until the distal end of the cannula assembly docks against the surface. The guide wire and the dilator are then removed from the dilator sheath, which remains and serves as the working cannula.

The percutaneous access incision may be made by one of several methods. Typically, under fluoroscopic guidance to appropriately maintain anterior/posterior alignment, the beveled tip at the distal end of a pin is advanced from the percutaneous entry point to the target site on the vertebral face, and into the bone by tapping the proximal end with a small mallet. For example, using fluoroscopic visualization, a stab incision may be made using a Steinmann pin (e.g. from between about 2 mm to about 4 mm in diameter and from between about 12" (305 mm) to about 14" (355 mm) in length). Alternatively, a finer-diameter "jamshidi" pin, such as those commercially available from, for example, Cardinal Health, Inc, in Dublin Ohio, is first advanced through soft tissue and muscle to create a working channel to the surgical site, followed by subsequent dilation to expand the diameter of the entry/targeted site of the working channel. Dilation may be achieved by advancement from the entry site of, for example, a 6 mm dilator that is tapered on its distal end and that is concentrically deployed within a dilator sheath, over the pin or pin. The dilator sheath provides a protected portal to the surgical site. That is, in one mode of use, a working cannula is maintained by the sheath, following dilation by the dilator which may then be removed from the sheath.

After ensuring that all of the stud assemblies 280 engaged with the various spacing landmarks and the slotted spacer bar 252 and the thumb screws 148 and 242 are tight to prevent motion of components relative to the cross bar 254 that the alignment of the external alignment line remains correct, a pin with drill bit is inserted into the working cannula 262. The bit is rotated manually or by a drill (not shown) to bore a pilot hole into the bone for subsequent receipt and insertion of the fixation screws.

Next, the fixation screw (sized to have a major diameter and head diameter slightly less than the inner diameter of the working cannula (e.g., dilator sheath) are deployed into and through the working cannula (either over a guide wire or retained on the distal end of a driver with a retention rod that engages a threaded bore in the distal end of the screw so it stays with the driver until released) oriented along the external alignment line for implantation of the first screw across the facet joint 742 on the first side of the vertebra 704.

Figure 20:
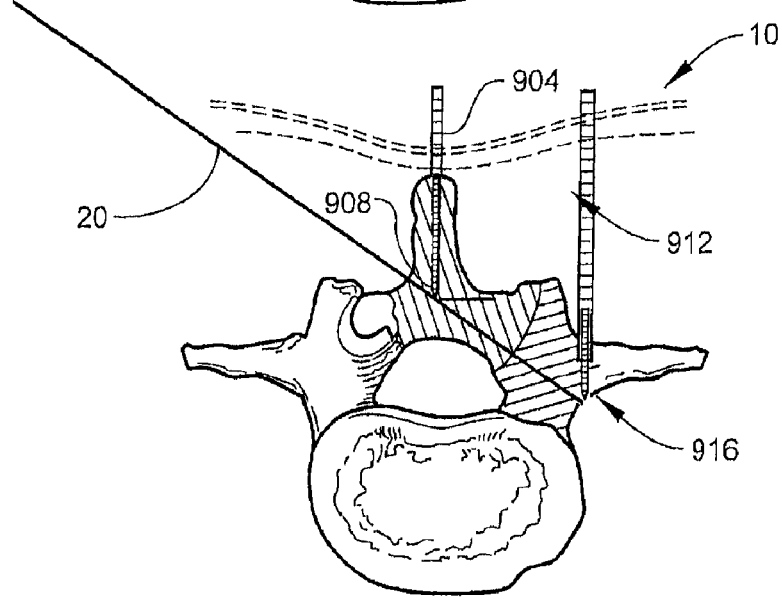
FIG. 20 is a cross-section view of the spine showing placement of guide pins to define an internal target path for delivery of a second translaminar facet screw.

Following deployment of fixation screw (translaminar facet screw) on the first side, the alignment jig may be disassembled and K-wire 912 removed while leaving K-wire 904 in spinous process 836. As indicated in FIG. 20, K-wire 912 is placed on the opposite side so the K-wire tips 908 and 916 define an internal alignment path 20. (Again, only the lower portions of the K-wires are show in FIG. 20). The process steps are repeated to deploy the second fixation screw.

With the second screw implanted, the working cannula is removed from the patient's body 10 and the alignment jig 100 is removed from the patient, and the incisions of the surgical site are closed.

It should be understood to those skilled in the art that the apparatus of the present disclosure may be used to implant a variety of screws using a transarticular (rather than translaminar) approach directly across the facet joints. Such an application could be accomplished by simply varying the placement of the K-wires to achieve the necessary screw trajectories. It is contemplated that the implantation of transarticular screws may be best accomplished by inserting the first K-wire into the lamina a few millimeters lateral of the spinous process rather than into the spinous process itself, and re-positioning the swivel cannula guide sub-assembly to aid with placement of direct (or transarticular) facet screws.

The alignment jig may be used to align the placement of screws either directly across the facet joints of adjacent vertebrae or indirectly across the facet joints through the lamina (i.e., translaminar) as both a primary mechanism for spinal fixation and as a secondary mechanism for fixation to augment anterior fusion or pedicle screw fixation instrumentation. It is contemplated that the alignment jig could be used in connection with the delivery of other therapies where an internal target path can be defined by guide pin tips and then an appropriate external alignment line established through the use of the alignment jig. These other therapies may include implantation of a variety of other orthopedic screws in the different parts of the spine as well as other bones. Significantly, the alignment jig provides for the accurate and repeatable placement of therapy such as the delivery of facet screws for fusing adjacent vertebrae in a minimally invasive procedure that saves time during surgery and is less traumatic to the patient. While an example of the use of an alignment jig has been given in the context of providing therapy to the spine, an alignment jig appropriately sized for the relevant geometry may be used for surgery in other parts of the body. Examples include surgery to the foot or the wrist where there is the need to align therapy with a number of anatomical features.

MATERIALS AND COMPONENTS

The term guide pin has been used throughout this disclosure. The term pin merits some additional description. A pin is a type of device frequently used in fixation of fractures or joints. A pin is in general thinner than a nail, screw or rod, but is generally thicker than a wire. Among the types of pins are, for example, the Knowles, Rush and Steinmann pins. Rush pins are round in cross section with a hooked end; this design helps prevent distal pin migration and aids in extraction. Steinmann pins may also be used to hold tension bands in place and provide rotational stability, or to create an access channel through soft tissue or bone. They may range in diameter from, for example, between about 1.5 mm to about 4 mm in diameter. Wires, known as "K-wires," or Kirschner-wires, are also a type of fracture or joint fixation device, which can be used in maintaining fracture fragments in correct position and in compression during healing or fusion, with or without cerclage or tension band wiring. They may also be used to create a relatively minimally-invasive access channel via dilation through soft tissue or bone. K-wires may range in diameters that are often (but not always) less than that of pins. In general, K-wires are less than about 0.062" (~1.6 mm) while dimensions that are greater than 0.062" may be described as Steinman pins.

In the context of the present disclosure the terms pins and K-wires are used interchangeably, unless otherwise indicated, or as otherwise would be obvious to one of ordinary skill in the art.

The guide pins may be either threaded or unthreaded, and fabricated, for example, from 300 series stainless steel. Examples of guide pins may be about 4" (~100 mm) in length, and from between about 0.032" (~1 mm) to about 0.062" (~1.6 mm), often about 0.042", in diameter.

K-wires that may be suitable for use with the present disclosure include elongate rods made of a biocompatible metal or other suitable material with an outer diameter of between about 1 mm to about 2 mm.

Except for their respective hinge pins, which may be fabricated from metal, such as stainless steel, the swivel guide pin sheath assembly 104 and the swivel cannula guide assembly 204 components may fabricated from any of a number of known suitable, structural, sterilizable, and preferably radiolucent polymers (able to be visualized via fluoroscopy, due to the addition of barium sulfate powder). Examples of suitable polymers include polysulfone, polyvinylidene fluoride (PVDF), polyethylene, PEEK, PTFE (e.g., Teflon™), nylon, ABS, polycarbonate, polypropylene, PVC, or the like, or composites thereof. The swivel guide pin sheath and the swivel cannula guide components of the assembly are fabricated from made from an acetal-based copolymer, such as Delrin™ obtained from the DuPont Company in Wilmington, Del., that is then injection-molded and/or machined.

In order to reduce the weight of certain components in the alignment jig, components may be made of a suitable graphite epoxy. The cross bar 254 may be made of any suitable polymer or metal.

In addition, the working cannula 262 (FIG. 14) may be fabricated as a polymeric bushing. The working cannula 262 may also be fabricated from a metal, such as machined from 300 series stainless steel alloy.

The drill may be a Steinmann pin fitted with a tip suitable for piercing, boring, or drilling. The drill may be a rod having a distal end having a fluted section with helical flutes and a proximal end with or without handle engaged at the proximal end of the rod. The drill tip may first be advanced into the bone by tapping, such as with a slap-hammer.

The helical flutes on the drill facilitate boring as the shaft is turned (either manually or by a power appliance, depending on the configuration of the drill used) in the appropriate direction to advance the drill distally into the working channel and into the vertebra. The drill is typically fabricated from hardened stainless steel or the like. The length of the drill typically ranges from about 12" (305 mm) to about 15" (380 mm), i.e. as needed based on the patient's anatomy and to extend beyond the proximal end of the working cannula. The drill diameter may be sized to fit through the working cannula. The drill diameter may be from between about 2 mm to about 5 mm (0.20"). The distal end of the drill may be used to finely and precisely penetrate the bone to extend the working channel into the spinal vertebra to the treatment area (e.g., translaminar to the facet joints), by inserting it into the lumen at the proximal end of the working cannula used as a protected portal, then the drill is advanced by turning the proximal end of the twist drill so that the helical flutes at the distal end of the drill progressively bore into the bone, forming a bore that may be from between about 2 mm to about 2.5 mm in diameter. The drill may be used to provide a pilot hole for the screw, which is pre-drilled in the bone. The major diameter of the screw threads may be larger than the diameter of the drill.

Translaminar facet screws (sometimes simply "fixation screws") may be between about 35 mm to about 65 mm, often between 45 mm to 60 mm in length, and with diameters of between about 0.120" (3 mm) to about 0.180" (4.5 mm) and often about 0.140" to about 0.160" (4 mm) are used. Fixation screws may be configured as elongate rods that have heads at one end and tapered tips at an oppositely disposed end. Fixation screws may have fully threaded shanks or lag type fixation screws may be used that are not fully threaded along the entire shank.

Fixation screws, as implantable components, may be fabricated from biocompatible orthopedic implant materials that are common medical grade materials, i.e., with substantial clinical history across a wide variety of orthopedic utilities that present no biocompatibility issues.

In the context herein, "biocompatible" refers to an absence of chronic inflammation response when or if physiological tissues are in contact with, or exposed to (e.g., wear debris) the materials and devices of the present disclosure.

The fixation screw may be cannulated along its longitudinal axis throughout its length, to enable delivery to the surgical site over a guide wire of about 1 mm in diameter and about 13" (300 mm) to about 16" (400 mm) in length.

The fixation screw is both delivered to the targeted site and then inserted into bone by driver configured with to engage and retain the fixation screw to the distal tip of the driver, such as shown in FIG. 14 in commonly assigned U.S. patent application Ser. No. 11/202,655 filed on Aug. 13, 2005, and subsequently published as United States Patent Application Publication US 2006/0058800A1., the relevant portions of which are herein incorporated into this document by reference. The rod driver engaging zone can be made in one of several configurations known to those of skill in the art to allow a driver to impart rotation to the rod. For example, the head end of the fixation screw can be configured as a female hex head suitable for driving with a driver having a corresponding male hex head. The head end of the fixation screw can also be configured for threaded engagement with a set of external threads from a retention rod included as part of the driver so that the fixation screw can be selectively engaged with the retention rod before insertion into the body and then disengaged from the retention rod after the fixation screw is at least partially inserted in to the bore in the vertebra.

The fixation screw rod drivers generally include elongate bodies (or shafts) and handles fabricated from stainless steel alloys, such as those described in ASTM F899-02 Standard Specifications for Stainless Steels for Surgical Instruments or, for example, 17-4 alloy where torque is a consideration, such as when driving components into bone. Similarly, for this reason, as well as to prevent transfer of dissimilar metallic elements to the implant which may contribute to electrochemical corrosion in-situ some driver tips may be fabricated from the same materials as the implantable translaminar facet screws (such as a titanium alloy as described, above).

GENERAL COMMENTS

One of skill in the art will recognize that alternative implementations set forth above are not universally mutually exclusive and that in some cases additional implementations can be created that implement two or more of the variations described above. In a like manner, one of skill in the art will recognize that certain aspects of the present invention can be implemented without implementing all of the teachings illustrated in any of the various disclosed implementations. Such partial implementations of the teachings of the present disclosure fall Within the claimed subject matter unless the claims are explicit in calling for the presence of additional elements from other teachings.

In order to promote clarity in the description, common terminology for components is used. The use of a specific term for a component suitable for carrying out some purpose within the disclosed invention should be construed as including all technical equivalents which operate to achieve the same purpose, whether or not the internal operation of the named component and the alternative component use the same principles. The use of such specificity to provide clarity should not be misconstrued as limiting the scope of the disclosure to the named component unless the limitation is made explicit in the description or the claims that follow.

In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

Those skilled in the art will recognize that the methods and apparatus of the present invention have many applications and that the present invention is not limited to the specific examples given to promote understanding of the present invention. Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalencies. Those unfamiliar with the legal tests for equivalency should consult with a person registered to practice before the United States Patent and Trademark Office.

What is claimed is:

1. An apparatus for aligning an external target path relative to an internal target path, the apparatus comprising:
    a first guide pin with a first distal tip to designate a first point on the internal target path;
    a second guide pin with a second distal tip to designate a second point on the internal target path;
    a first hinged mechanism connected to the first guide pin and to a reference bar with a first hinge between the first guide pin and the reference bar;
    a second hinged mechanism connected to the second guide pin and to the reference bar with a second hinge between the second guide pin and the reference bar, the second hinged mechanism capable of movement along the reference bar to alter a distance between the connection of the first hinged mechanism to the reference bar and the connection of the second hinged mechanism to the reference bar;
    spacing landmarks on the first and second hinged mechanisms sufficient to allow a creation of a first parallelogram involving the first and second hinged mechanisms such that the reference bar is placed parallel to the internal target path; and
    an external target path guide connected to a hinged parallelogram, the hinged parallelogram connected to the reference bar so that the external target path guide is always parallel to the reference bar but may move relative to the reference bar,
    whereby placing the hinged parallelogram parallel to either guide pin after creation of the first parallelogram sets the external target path guide to establish an external target path with a slope that is equal to a slope of the internal target path and a predictable offset from co-linear with the internal target path.

2. The apparatus of claim 1 wherein the predictable offset is zero and the external target path guide establishes an external target path that is co-linear with the internal target path.

3. The apparatus of claim 1 wherein the predictable offset includes a component orthogonal to a plane containing both centerlines of the first and second guide pins.

4. The apparatus of claim 1 wherein the predictable offset includes a component that varies with an angle formed between the first guide pin and the reference bar.

5. The apparatus of claim 1 wherein the connection of the hinged parallelogram to the reference bar can move relative to the reference bar.

6. The apparatus of claim 1 wherein the external target path guide contains a channel, the channel has a centerline, and the external target path is located at the centerline of the channel.

7. A method for translating a target path from a dorsal portion of a spine inside a body to outside the body to allow for a percutaneous working cannula to be positioned parallel to the target path; the method comprising:
    positioning a first pin tip in the body to define one point on the target path, the first pin tip located at a distal end of a first spinal guide pin;
    positioning a second pin tip in the body to define a second point on the target path, the second pin tip located at a distal end of a second spinal guide pin;
    engaging a proximal end of the first spinal guide pin with a first swivel guide pin sheath assembly comprising:
    a first pin engager hingedly connected to
    a first slider,
    engaging a proximal end of the second spinal guide pin with a second swivel guide pin sheath assembly comprising:

a second pin engager hingedly connected to a second slider, engaging a cross bar with first and second sliders so that the first and second sliders are substantially constrained by the cross bar to limit relative movement of the first and second sliders to one another to translation along a long axis of the cross bar;

capturing a distance between a first distance landmark on the first pin engager and a second distance landmark on the second pin engager;

replicating the captured distance between a third distance landmark in the first slider and a fourth distance landmark in the second slider;

affixing at least one of the first or second slider to the cross bar so that the first slider cannot move relative to the second slider along the cross bar;

engaging a slider portion of a swivel cannula guide assembly with the cross bar and placing a guide block portion of the swivel cannula guide assembly in proximity with an outside of the body, the guide block portion of the swivel cannula guide assembly connected via at least two joints to the swivel cannula guide assembly;

capturing a spacing distance between a distance landmark in one of the first or second pin engagers and a fifth distance landmark on part of the swivel cannula guide assembly; and imposing the captured spacing distance between a distance landmark in a corresponding slider selected from the first and second sliders hingedly connected to that pin engager and a sixth distance landmark in the slider portion of the swivel cannula guide assembly such that the swivel cannula guide assembly is substantially parallel to the first and second spinal guide pins and a centerline of a bore through the guide block portion of the swivel cannula guide assembly is substantially parallel to the target path defined by the first pin tip on the first spinal guide pin and the second pin tip on the second spinal guide pin.

8. The method of claim 7 wherein:

the first pin tip and the second pin tip are placed across a pair of adjacent vertebrae with a more cephalad, upper vertebra and a more caudal, lower vertebra, the first pin tip is placed into a spinous process in the upper vertebra and the second pin tip is placed in a first transverse process in a first side of the lower vertebra.

9. The method of claim 7 wherein:

the engaging of the cross bar with first and second slider so that the first and second sliders are substantially constrained by the cross bar to limit relative movement of the first and second sliders to one another to translation along a long axis of the cross bar includes passing a portion of the cross bar through a channel in the first slider and passing a portion of the cross bar through a channel in the second slider; and the engaging a slider portion of a swivel cannula guide assembly with the cross bar includes passing a portion of the cross bar through a channel in the slider portion of the swivel cannula guide assembly.

10. The method of claim 7 wherein the centerline of the bore through the guide block portion of the swivel cannula guide assembly is substantially co-linear with the first pin tip on the first spinal guide pin and the second pin tip on the second spinal guide pin.

11. The method of claim 7 wherein the centerline of the bore through the guide block portion of the swivel cannula guide assembly is parallel but not co-linear with the first pin tip on the first spinal guide pin and the second pin tip on the second spinal guide pin so that a fixation means may be introduced that is substantially coaxial with the centerline of the bore without the fixation means contacting the first pin tip or the second pin tip.

12. The method of claim 7 wherein the first distance landmark on the first pin engager is a bore hole such that an elongated protrusion can be inserted into the first pin engager.

13. The method of claim 7 wherein the first distance landmark is an elongated protrusion that extends outward substantially perpendicular from a surface of the first pin engager.

14. The method of claim 7 wherein:

engaging the proximal end of the first spinal guide pin with the first swivel guide pin sheath assembly includes seating the proximal end of the first spinal guide pin in a cavity in the first pin engager;

engaging the proximal end of the second spinal guide pin with the second swivel guide pin sheath assembly includes seating the proximal end of the second spinal guide pin in a cavity in the second pin engager; and a first distance from the first pin tip on the seated first guide pin to a centerline of a hinged connection between the first pin engager and the first slider equals a second distance from the second pin tip on the seated second guide pin to a centerline of a hinged connection between the second pin engager and the second slider.

\* \* \* \* \*